(12) United States Patent
Watkins

(10) Patent No.: US 7,145,052 B1
(45) Date of Patent: Dec. 5, 2006

(54) DECONTAMINATION APPARATUS AND METHODS

(75) Inventor: William B. Watkins, Tequesta, FL (US)

(73) Assignee: United Technologies Corporation, Hartford, CT (US)

( * ) Notice: Subject to any disclaimer, the term of this patent is extended or adjusted under 35 U.S.C. 154(b) by 1 day.

(21) Appl. No.: 10/952,899

(22) Filed: Sep. 28, 2004

(51) Int. Cl.
*A62D 3/00* (2006.01)
*A61L 2/08* (2006.01)

(52) U.S. Cl. .................... 588/320; 588/299; 422/28

(58) Field of Classification Search ............. 588/320, 588/299, 401, 405–409, 900, 901
See application file for complete search history.

(56) References Cited

U.S. PATENT DOCUMENTS

| | | | |
|---|---|---|---|
| 4,466,556 A | | 8/1984 | Sochting |
| 4,551,092 A | | 11/1985 | Sayler |
| 4,909,999 A | * | 3/1990 | Cummings et al. ......... 422/298 |
| 5,872,359 A | * | 2/1999 | Stewart et al. ......... 250/339.12 |
| 5,876,664 A | * | 3/1999 | Childers et al. ............... 422/28 |
| 6,077,480 A | * | 6/2000 | Edwards et al. ............... 422/28 |
| 6,532,741 B1 | | 3/2003 | Watkins |
| 6,606,853 B1 | * | 8/2003 | Watkins ....................... 60/259 |
| 6,652,248 B1 | | 11/2003 | Watkins et al. |
| 2002/0114727 A1 | | 8/2002 | McVey et al. |
| 2002/0159915 A1 | * | 10/2002 | Zelina et al. ................... 422/3 |
| 2004/0057868 A1 | | 3/2004 | McVey et al. |
| 2004/0215046 A1 | | 10/2004 | McVey et al. |
| 2005/0084415 A1 | * | 4/2005 | McVey et al. ................. 422/28 |

FOREIGN PATENT DOCUMENTS

| | | | |
|---|---|---|---|
| WO | WO 00/15306 | * | 3/2000 |
| WO | WO 02/066082 | * | 8/2002 |

OTHER PUBLICATIONS

European Search Report for EP Patent Application No. 05255579.4.

* cited by examiner

*Primary Examiner*—Colleen P. Cooke
(74) *Attorney, Agent, or Firm*—Bachman & LaPointe, P.C.

(57) ABSTRACT

Decontamination apparatus and methods involve catalytic decomposition of hydrogen peroxide to drive additional hydrogen peroxide to a contaminated location.

30 Claims, 4 Drawing Sheets

US 7,145,052 B1

DECONTAMINATION APPARATUS AND METHODS

BACKGROUND OF THE INVENTION

The invention relates to decontamination. More particularly, the invention relates to decontamination against chemical and biological agents.

Well developed fields exist regarding the decontamination of areas contaminated with chemical and biological agents. Various techniques involve thermal decontamination. Some are typically useful for decontaminating thermally robust contaminated locations such as the exposed surfaces of a military vehicle. For example, U.S. Pat. No. 4,551,092 to Sayler discloses a jet engine decontamination system. In such a system, the jet exhaust is directed to the contaminated surfaces and heats them sufficiently to decompose chemical agents and kill biological agents. Various such systems are vehicle-mounted permitting the jet exhaust to be controllably swept over the surfaces to be contaminated.

More recently, concerns regarding laboratory and factory accidents, bio-terrorism, and the like encouraged development of principally chemical decontamination systems for decontaminating less robust (and often larger) locations. For example, the interior of an entire building or a portion thereof (e.g., a room) may need to be decontaminated. Exemplary chemical decontamination systems have typically involved use of chlorine (e.g., chlorine dioxide). However, use of chlorine dioxide raises certain safety considerations. Accordingly, use of hydrogen peroxide vapor for decontamination has been proposed. International Patent Publication WO 02/066082 of Steris, Inc. et al. discloses a flash vaporizer for providing antimicrobial hydrogen peroxide. Chemical systems may also be used in direct spray modes in lieu of the thermal systems. For example, it has been proposed to use a chemical system for the in situ decontamination of jet aircraft engines.

Separately, catalytic systems have been developed to decompose hydrogen peroxide into water and oxygen (e.g., to provide oxygen for use in rocket propulsion). For example, U.S. Pat. No. 6,532,741 to Watkins and U.S. Pat. No. 6,652,248 to Watkins et al. disclose such catalytic systems.

SUMMARY OF THE INVENTION

One aspect of the invention involves a decontamination method. At least a first flow of hydrogen peroxide is directed to a catalytic reactor. The first flow is passed through a catalyst so as to decompose at least a portion of the first flow into water and oxygen. A discharge flow of the water and oxygen and additional hydrogen peroxide is directed to a contaminated location so as to provide a decontamination.

Another aspect of the invention involves a decontamination apparatus. A vessel contains a supply of hydrogen peroxide. A catalytic reactor is coupled to the vessel to receive a first flow and at least partially decompose hydrogen peroxide from the first flow into decomposition products. An outlet is positioned to direct a discharge flow containing the decomposition products and undecomposed hydrogen peroxide to a contaminated location.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Like reference numbers and designations in the various drawings indicate like elements.

DETAILED DESCRIPTION

Figure 1:
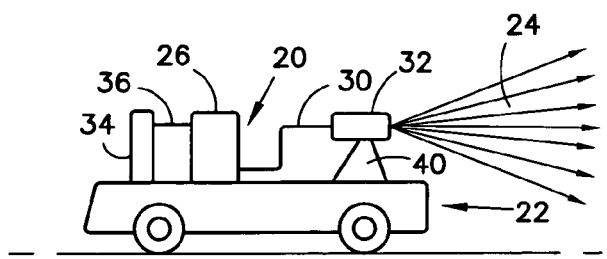
FIG. 1 is a schematic view of a first decontamination system.

A catalytic decomposition system may decompose a first hydrogen peroxide flow or portion thereof and help drive an additional non-decomposing hydrogen peroxide flow or portion for decontamination. FIG. 1 shows a first exemplary decontamination system 20 mounted on a vehicle 22 (e.g., a self-propelled or towed wheeled or tracked vehicle). The system 20 delivers an output/discharge flow or stream 24 (e.g., essentially a gaseous mixture) containing a quantity of hydrogen peroxide effective for decontamination use. The exemplary system 20 includes a vessel (e.g., a tank) containing a relatively high concentration of hydrogen peroxide (e.g., in excess of a 70% solution (weight percent unless noted), more advantageously in excess of a 90% solution, and most advantageously in excess of a 95% solution, such as an approximately 98% solution). The hydrogen peroxide is delivered through a conduit 30 to a catalytic reactor 32. This flow from the tank may be a blow-down flow caused by a pressurant gas (e.g., nitrogen). An exemplary pressurant gas is stored in a separate vessel or tank 34 coupled to a headspace of the tank 26 via a conduit 36. Valves (not shown) may control the flow through the conduits 30 and 36 and may be actuated by a control system (also not shown). The reactor 32 and/or an outlet therefrom may be capable of orientational and/or positional changes such as via an actuator system 40 (e.g., electromechanical, hydraulic, or pneumatic) to permit aiming of the stream 24 such as for sweeping a discharge pattern over a larger area to be contaminated.

The catalytic reaction in the reactor 32 converts just a portion of the hydrogen peroxide delivered to the reactor. For example, with a reactor input flow of 98% hydrogen peroxide, sufficient hydrogen peroxide may be decomposed into water vapor and oxygen that the discharge stream 24 will have a hydrogen peroxide content of approximately 35% (at a temperature of about 260° C. (500° F.) compared with about 950° C. (1750° F.) for full decomposition). The decomposition releases energy which heats and further expands the reaction products (in addition to the 50% molar expansion). The expansion may substantially drive the stream 24 including the entrained unreacted hydrogen peroxide. A broader range of the percentage of the hydrogen peroxide which may be decomposed may result in an output stream having 10–75% hydrogen peroxide. A narrower range is 15–35%. An exemplary stream may have at least 30%. An exemplary temperature of the stream 24 is 170–280° C. (800–1000° R). An exemplary flow rate may depend upon the particular application (e.g., 0.05–9 kg/s). With a system sized for decontaminating typical military vehicles, an exemplary flow rate may be in the range of 1–3 kg/s. An exemplary system for open area decontamination may have a rate of 2–5 kg/s per reactor. In various implementations, there may be a mass flow rate of 2–9 kg/s for a duration of at least 10 s. An exemplary reactor is self-heating due to the catalytic reaction and thus lacking external heating (e.g., electric) at least during post-start-up conditions. An external start-up preheater for the reactor is an option.

As noted above, the stream 24 may be directly against a surface to be decontaminated or may be directed for area decontamination (e.g., of a field, street, and the like). An alternate open air use is more of a point defense operation with the stream 24 directed against an incoming cloud of biological or chemical warfare agent or counterstream against an incoming stream of such agent (a contaminant stream). Agents may include nerve agents, blister agent, live bacteria, and bacterial spores. One particular example is anthrax.

Figure 2:
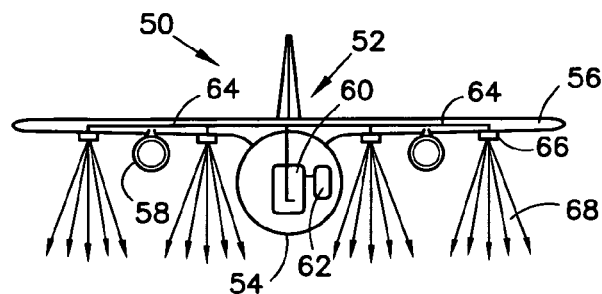
FIG. 2 is a schematic view of a second decontamination system.

FIG. 2 shows another application wherein such a system 50 is mounted in an aircraft 52 having a fuselage 54. In an exemplary manned fixed-wing aircraft having a main wing 56 bearing engine nacelles 58, the hydrogen peroxide and pressurant tanks 60 and 62 may be contained within the fuselage. A conduit network 64 extends from the hydrogen peroxide tank to a number of separate reactors 66 mounted along the wing (either externally or internally) and discharging streams 68. The streams may be discharged in a generally downward direction for area decontamination (e.g., of open fields or other outdoor areas). An exemplary number of separate reactors is 2–8 with at least one on each of the port and starboard sides of the wing. Unmanned and rotary wing aircraft are alternate platforms as are less integrated systems (e.g., substantially externally mounted systems).

Figure 3:
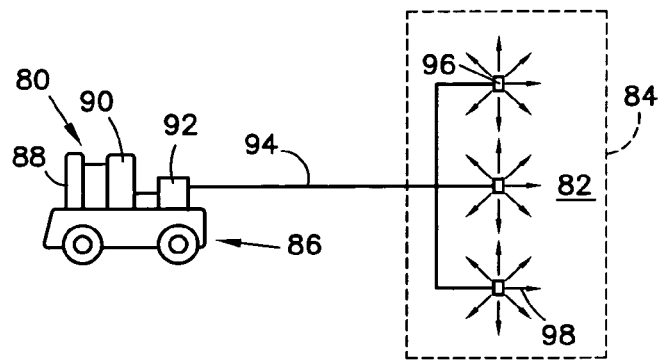
FIG. 3 is a schematic view of a third decontamination system.

FIG. 3 shows a system 80 for decontaminating an enclosed area 82 (e.g., one or more rooms within a building 84). The system may be mounted on a self-propelled or towed wheeled or tracked vehicle 86 and may include pressurant and peroxide tanks 88 and 90 and a reactor 92 similarly connected as those of the system 20. In the illustrated embodiment, rather than directly discharging an airborne stream, the reactor is coupled to a discharge conduit network 94 which may include several branches terminating in several nozzles 96 discharging respective streams 98. These nozzles may be configured to distribute relatively diffuse (e.g., omnidirectional) gaseous streams 98. The individual nozzles may be located in separate rooms, a common room, or may be coupled to a building HVAC system providing distribution of the hydrogen peroxide. In another variation, multiple reactors remote of the vehicle could replace the multiple nozzles in a plumbing arrangement similar to that of the system 50. In yet another arrangement wherein the vehicle is sufficiently small (e.g., a hand-movable cart) the vehicle may be brought into the building or room to be decontaminated. Relatively small flow rates may be appropriate for decontamination of confined internal spaces. The confinement retains the hydrogen peroxide for a duration after the flow is shut-off thereby increasing effectiveness. For example, to decontaminate the interior of a vehicle such as an armored vehicle or an ambulance, a much smaller amount is required than to decontaminate the exterior. For such an internal vehicular decontamination, a flow rate of about 0.02–0.1 kg/s for a period of about 5–10 s could substantially fill the interior space. With the vehicle sealed, the hydrogen peroxide could largely persist for a period of 5–10 minutes or longer to provide the effective decontamination.

Figure 4:
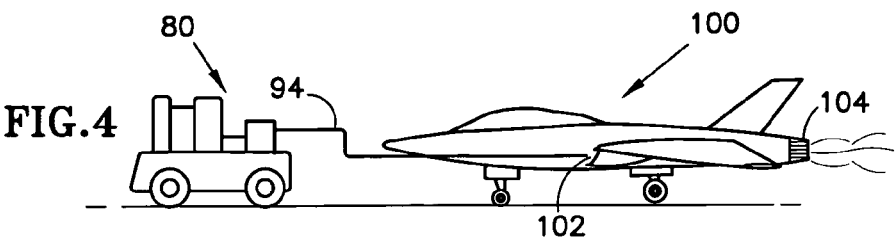
FIG. 4 is a schematic view of a fourth decontamination system.

FIG. 4 shows the system 80 being used to decontaminate the engine(s) of an aircraft 100. The conduit network 94 is positioned to discharge the hydrogen peroxide streams into one or more engine intakes (inlets) 102 forcing the hydrogen peroxide through the engine and ultimately out an engine exhaust nozzle 104. This may be performed while the engine is not running (although its spools may be fixed or rotating (e.g., induced by the hydrogen peroxide flow)). In such a system, the nozzle(s) may be mounted to a temporary cover placed over the engine intake(s) or one or more ducts may engage the intake(s) to guide the discharge flow.

Figure 5:
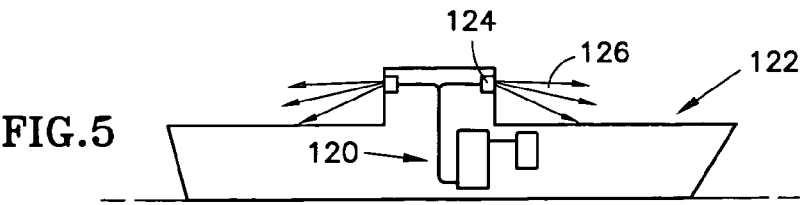
FIG. 5 is a schematic view of a fifth decontamination system.

FIG. 5 shows a system 120 aboard a ship 122. The system 120 may have one or more central hydrogen peroxide and pressurant tank groups feeding one or more central and/or remote reactors 124 (directly or via additional conduits) discharging streams 126 to decontaminate exposed surfaces of the ship. Other such variations on decontamination of a first ship or land vehicle by a second ship or land vehicle are possible.

Suitable reactors may be formed in a variety of ways. One example is the catalyst bed assembly of Watkins et al. noted above (the disclosure of which is incorporated by reference herein as if set forth at length). With such a system, the portion of the hydrogen peroxide flow to be decomposed may pass through the catalyst bed while a remaining portion passes around and cools the catalyst bed and/or a housing. Alternatively, or in combination, the catalyst bed may be relatively undersized (e.g., so as to not decompose substantially all the hydrogen peroxide passing through the catalyst bed). Exemplary catalysts include: silver (e.g., formed as a screen or screen plating); and silver-based alloys. However, any catalyst that is useful in decomposing the hydrogen peroxide could be used.

Figure 6:
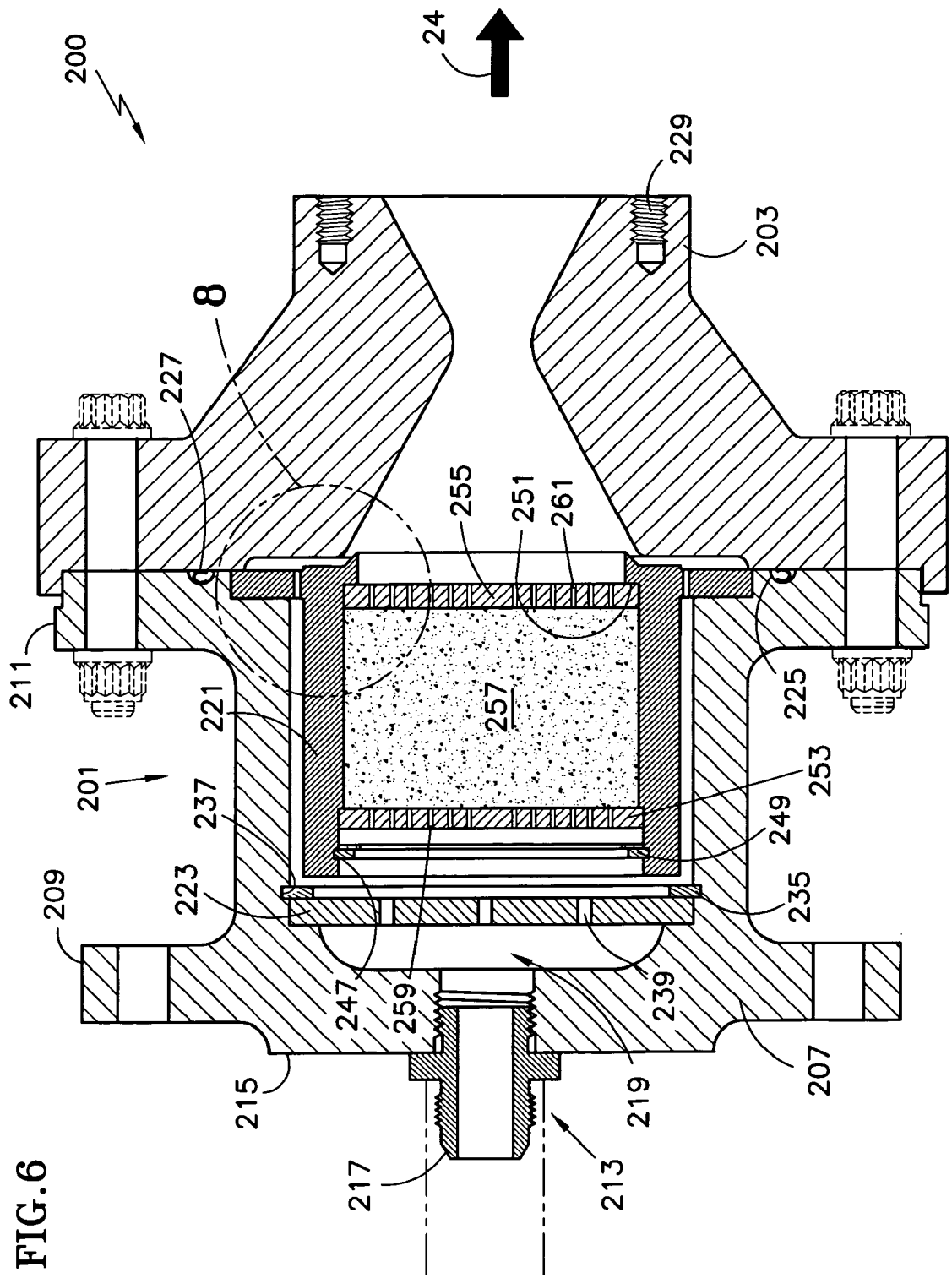
FIG. 6 is a longitudinal cross-sectional view of a catalyst bed assembly of a decontamination system.

FIG. 6 shows details of a catalyst bed assembly 200 taken from Watkins et al. The catalyst bed assembly 200 includes a catalyst bed section 201 and a nozzle section 203. The nozzle section 203 secures to the catalyst bed section 201 with suitable fasteners 205. As an example, the catalyst bed section 201 has an inner diameter of approximately 10 cm when dimensioned for an exemplary use in a medium flow rate application such as building interior decontamination.

The nozzle section 203 resides at the downstream, or outlet, end of the catalyst bed 201. The nozzle 203 receives the discharge from the catalyst bed section 201. The nozzle accelerates the discharge from the catalyst bed section 201 to form the exhaust stream (e.g., 24 et al.). Although shown as a convergent-divergent nozzle, other outlet structures are possible.

The nozzle section 203 can have threaded openings 229 for securing to any downstream component (e.g., the conduit assemblies 64 et al.). Also, the nozzle section 203 could be made from any suitable material, such as a high temperature, non-catalytic aerospace alloy.

The catalyst bed section 201 includes a catalyst can (cannister) 221 within an outer housing 207. The outer housing 207 can be a cylindrical pipe having flanges 209 and 211 to secure the catalyst bed section 201 to other components (e.g., the associated vehicle, aiming actuators, or the like). However, other arrangements are possible. The outer housing 207 could be made from any suitable material, such as a high temperature, non-catalytic aerospace alloy.

The exemplary outer housing 207 secures to the nozzle section 203 using fasteners 205. The flange 211 may include an annular groove 225 within which a C-shaped (in cross-section) annular metal seal 227 resides. The seal 227 keeps the hydrogen peroxide from escaping from the joint between the catalyst bed section 201 and the nozzle section 203. Although described as a metallic C-shaped annular seal, any suitable seal or sealing arrangement could be used.

The exemplary outer housing 207 includes a threaded opening 213 in an upstream face 215. The opening receives a correspondingly threaded coupling 217 to create an inlet. The coupling 217 secures to the supply conduit (e.g., 30 et al., shown in phantom in FIG. 6) supplying hydrogen peroxide to the catalyst bed assembly 200.

Figure 7:
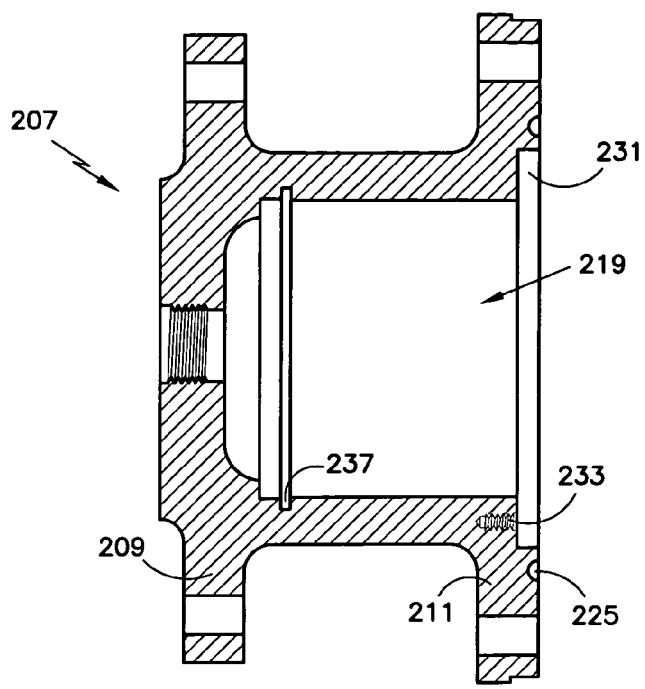
FIG. 7 is a cross-sectional view of an outer housing of the catalyst bed assembly of FIG. 6.

The exemplary outer housing 207 includes an open interior 219. The open interior 219 has a suitable size to receive the catalyst can 221. The exemplary outer housing 207 has an annular shoulder 231 (FIG. 7) in which a portion of the catalyst can 221 rests. The outer housing 207 also may have at least one threaded opening 233 for securing the catalyst can 221 on the shoulder 231 with a suitable fastener (not shown).

A first pressure baffle 223 resides within the open interior 219 of the outer housing 207. The pressure baffle 223 is preferably made from a high temperature, non-catalytic aerospace alloy. The baffle 223 has an array of openings 239 therethrough. Exemplary openings 239 have a diameter of approximately 1–2 mm. However, other sizes, numbers and arrangements of the apertures could be used to achieve a suitable result. A ring 235 placed in an annular groove 237 on the inner surface of the outer housing 207 retains the pressure baffle 223 within the outer housing 207.

The baffle 223 reduces the pressure of the liquid hydrogen peroxide in the direction of flow. In other words, the pressure of the hydrogen peroxide downstream of the baffle 223 is less than the pressure of the hydrogen peroxide upstream of the baffle.

As will be described in more detail below, in the exemplary embodiment, neither the outer housing 207 nor the nozzle section 203 require any cooling lines to manage the heat generated in the catalyst can 221 during decomposition of the hydrogen peroxide. Rather, a bypass flow of hydrogen peroxide (i.e., hydrogen peroxide that does not enter the catalyst bed) may cool the outer housing 207 and the nozzle section 203.

Figure 8:
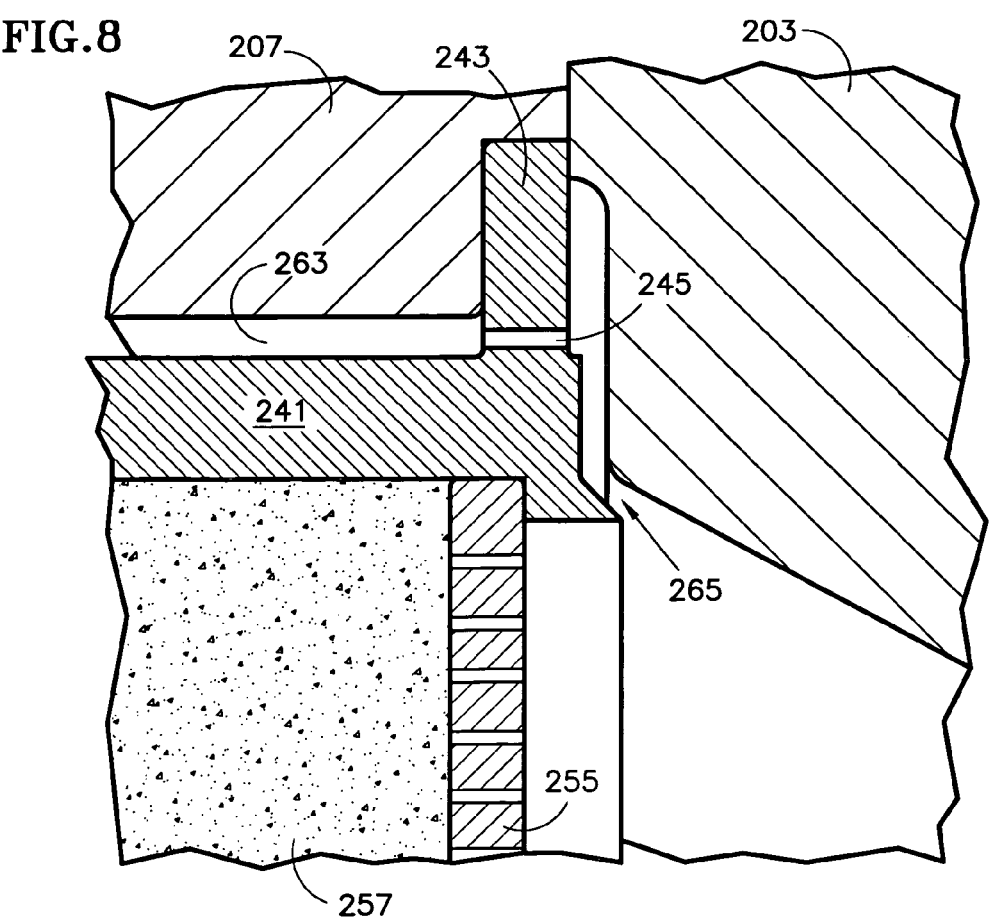
FIG. 8 is a detailed cross-sectional view of a downstream end portion of the catalyst bed assembly of FIG. 6.

The catalyst can 221 is preferably made from a suitable material, such as a high temperature, non-catalytic aerospace alloy. The exemplary catalyst can 221 has a cylindrical outer wall 241 (FIG. 8) and downstream end flange 243. The flange 243 includes a plurality of bypass apertures 245.

The interior of the exemplary catalyst can 221 has an annular groove 247 (FIG. 6) adjacent the upstream end. The groove 247 receives a metal ring 249. The downstream end of the catalyst can 221 includes an annular internal shoulder 251. The contents within the catalyst can 221 are retained between the metal ring 249 and the shoulder 251 and include: a second pressure baffle 253; a third pressure baffle 255; and catalyst material 257 forming a catalyst bed therebetween. The second pressure baffle 253 is located adjacent the ring 249. The second pressure baffle 253 is also preferably made from a high temperature, non-catalytic aerospace alloy. The second pressure baffle 253 has an array of openings 259 therethrough. An exemplary baffle 253 has an outer diameter of approximately 7 cm and the openings 259 have a diameter of approximately 2.4 mm. However, other sizes, numbers and arrangements of the apertures 259 could be used to achieve a suitable result.

The ring 249 placed in the annular groove 247 retains the pressure baffle 253 in the catalyst can 221. The baffle 253 serves to reduce the pressure of the liquid hydrogen peroxide in the direction of flow. In other words, the pressure of the hydrogen peroxide downstream of the baffle 253 is less than the pressure of the hydrogen peroxide upstream of the baffle.

The third pressure baffle 255 rests against the shoulder 251. The third pressure baffle 255 is also preferably made from a high temperature, non-catalytic aerospace alloy. The third press baffle 255 has an array of openings 261 therethrough. Preferably, the baffle 255 has an outer diameter of approximately 7 cm and the openings 261 have a diameter of approximately 2 mm. However, other sizes, numbers and arrangements of the apertures 261 could be used to achieve a suitable result.

Once the nozzle section 203 is secured to the catalyst bed section 201 and the supply pipe of hydrogen peroxide is secured to the coupling 217, the catalyst bed assembly 200 is ready to decompose the hydrogen peroxide. In an exemplary implementation, the supply of hydrogen peroxide enters the catalyst can 221 from the supply pipe with a diameter of approximately 8 cm at a flow rate of approximately 2–4 kg per second and a temperature of approximately 25° C. The catalyst material 257 decomposes the liquid hydrogen peroxide into water vapor, oxygen and heat. Other temperatures, flow rates and supply pipe sizes could be used to achieve a desired exhaust stream. Within the catalyst can 221, a 98% hydrogen peroxide would decompose into water vapor and oxygen at approximately 6.9 MPa (100 psi) and 945° C. (2192° R).

In order to withstand such high temperatures without using complex and heavy cooling schemes, the catalyst bed assembly 200 is designed so that a portion of the supply of hydrogen peroxide bypasses the catalyst can 221. An annular gap/passageway 263 (FIG. 8) exists between the outer housing 207 and the catalyst can 221. The bypass liquid hydrogen peroxide fills and flows downstream through the annular gap 263 and serves to cool the catalyst can 221. The liquid hydrogen peroxide in the annular gap 263 also limits heat build-up in the outer housing 207. The exemplary annular gap 263 terminates at the downstream flange 243 of the catalyst can 221. However, the bypass hydrogen peroxide, upon reaching the flange 243, passes through the apertures 245 in the flange 243. The amount of bypass could be controlled by the size of the annular gaps 263, 265, or by the number and the size of the apertures 245.

Because the nozzle section 203 is likewise exposed to the heat created by the decomposition of the hydrogen peroxide in the catalyst can 221, heat build-up in the nozzle section 203 should also be controlled. Similar to the annular gap 263, a gap 265 (FIG. 8) exists between the nozzle section 203 and the catalyst can 221 at the downstream end of the catalyst can 221. Preferably, the liquid hydrogen peroxide provides film cooling along the interior surface of the nozzle section 203 while traveling through the nozzle section 203.

Figure 9:
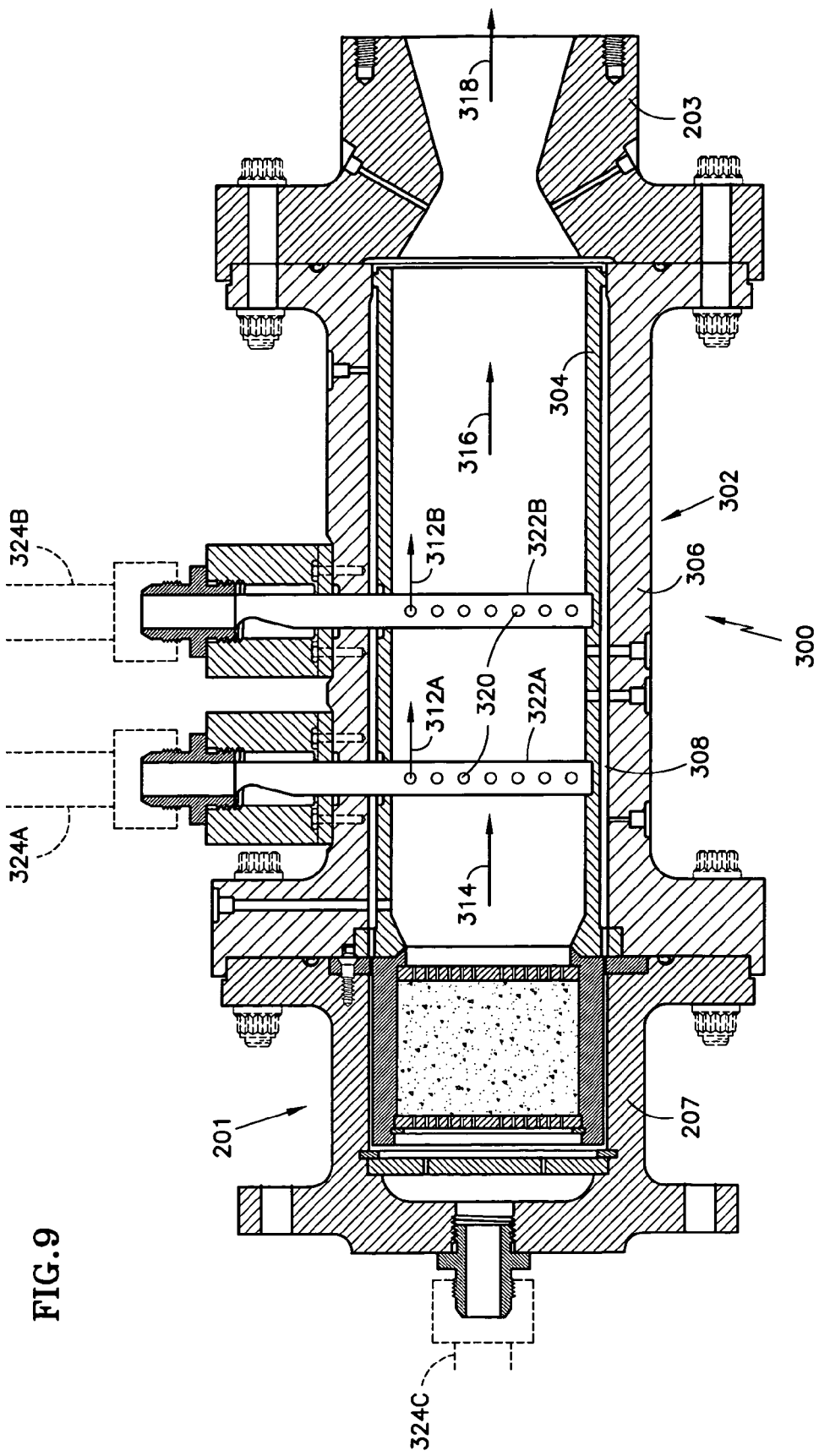
FIG. 9 is a longitudinal cross-sectional view of an alternate catalyst bed assembly.

FIG. 9 shows a catalyst bed assembly 300 wherein, relative to the assembly 200, an intermediate mixing section 302 intervenes between the catalyst bed section 201 and the nozzle section 203 as disclosed in Watkins. The mixing section 302 includes concentric inner and outer housing sections 304 and 306, respectively, defining an annular space/passageway 308 therebetween. The passageway 308 forms a continuation of the cooling passageway 263. The exemplary mixing section facilitates the introduction of supplemental hydrogen peroxide flows 312A and 312B to mix with the flow 314 exiting the catalyst bed to dilute/cool that flow to form a diluted flow 316 which finally mixes with the cooling flow to form the discharge flow 318. The exemplary flows 312A and 312B are expelled from apertures 320 in respective spray bars 322A and 322B. To feed the spray bars, the hydrogen peroxide feed conduit (e.g., 30 et al.) is split into branches, with branches 324A and 324B feeding the respective spray bars and a branch 324C feeding the catalyst bed. Flow through each of the branches may be controlled via an associated valve (not shown) actuated by the control system (not shown). Flow rates through the various branches may, in view of any start-up or cool-down considerations, control the total flow rate and the discharge composition and temperature.

The introduction of the flows 312A and 312B downstream of the catalyst bed (and distinguished from the cooling flow portion passing through the gap) adds further variables which may be used to achieve a desired output. For example, if substantially all the hydrogen peroxide passing through the catalyst bed is decomposed then it is likely that the decomposition products will cause partial decomposition of the hydrogen peroxide from the flows 312A and 312B as the latter cool the flow 314. To achieve a desired hydrogen peroxide concentration in the discharge flow 318, the supplemental/bypass flows 312A and 312B, in combination, would represent a greater mass flow than the hydrogen peroxide in the discharge stream 318. For example, in one implementation, approximately 95% of the third branch 324C hydrogen peroxide flow enters the catalyst can as a first flow for decomposition by the catalyst material. The remaining 5% of the hydrogen peroxide bypasses and may cool the catalyst bed assembly and mixing section. Substantially all the first flow may be decomposed. The combined mass flow rates through the branches 324A and 324B could be an exemplary 1–5 times of that through the branch 324C, more narrowly 2–3 times. About half or more of the hydrogen peroxide flowing through the branches 324A and 324B could decompose upon encountering the catalyst output flow 314. Overall bypass to through-catalyst flow rates could be similar.

In operation, the hydrogen peroxide and pressurant tanks may need to be frequently refilled (e.g., after each mission for an airborne system, or a given number of uses for other systems). The catalyst can may need replenishment or replacement less frequently, if at all.

One or more embodiments of the present invention have been described. Nevertheless, it will be understood that various modifications may be made without departing from the spirit and scope of the invention. For example, various catalytic technologies may be adopted. Additionally, various system parameters may be tailored to particular applications. Accordingly, other embodiments are within the scope of the following claims.

What is claimed is:

1. A decontamination method comprising:
    directing at least a first flow of hydrogen peroxide to a catalytic reactor;
    passing said first flow through a catalyst so as to decompose at least a portion of the first flow into water and oxygen; and
    directing a discharge flow of said water and oxygen and additional hydrogen peroxide to a contaminated location so as to provide a decontamination, said first flow passing from a vessel of said hydrogen peroxide to said reactor without passing through said contaminated location.

2. The method of claim 1 wherein:
    the discharge flow is directed essentially as a gaseous mixture.

3. A decontamination method comprising:
    directing at least a first flow of hydrogen peroxide to a catalytic reactor;
    passing said first flow through a catalyst so as to decompose at least a portion of the first flow into water and oxygen; and
    directing a discharge flow of said water and oxygen and additional hydrogen peroxide to a contaminated location so as to provide a decontamination,
wherein:
    the additional hydrogen peroxide comprises hydrogen peroxide from a bypass portion of the first flow, bypassing catalytic interaction with the catalyst, but cooling the catalyst.

4. The method of claim 3 wherein:
    the additional hydrogen peroxide further comprises hydrogen peroxide from a second bypass portion of the first flow, bypassing catalytic interaction and cooling interaction with the catalyst, but cooling an output from the catalyst.

5. The method of claim 3 wherein:
    the bypass portion flows along an essentially annular passageway surrounding the catalyst.

6. The method of claim 1 wherein:
    the additional hydrogen peroxide comprises undecomposed hydrogen peroxide from the first flow having passed through a bed of the catalyst.

7. A decontamination method comprising:
    directing at least a first flow of hydrogen peroxide to a catalytic reactor;
    passing said first flow through a catalyst so as to decompose at least a portion of the first flow into water and oxygen; and
    directing a discharge flow of said water and oxygen and additional hydrogen peroxide to a contaminated location so as to provide a decontamination,
wherein:
    expansion due to decomposition of said portion substantially drives said discharge flow.

8. The method of claim 1 wherein:
    the first flow comprises at least 70% hydrogen peroxide by weight; and
    the discharge flow comprises at least 30% hydrogen peroxide by weight.

9. The method of claim 1 wherein:
    the first flow comprises at least 95% hydrogen peroxide by weight.

10. The method of claim 1 wherein:
    the reactor is only catalytically heated, lacking supplemental heating.

11. A decontamination method comprising:
    directing at least a first flow of hydrogen peroxide to a catalytic reactor;
    passing said first flow through a catalyst so as to decompose at least a portion of the first flow into water and oxygen; and
    directing a discharge flow of said water and oxygen and additional hydrogen peroxide to a contaminated location so as to provide a decontamination,
wherein:
    the directing at least the first flow directs a plurality of flows to a plurality of reactors from a common hydrogen peroxide storage vessel.

12. The method of claim 1 wherein:
    the contaminated location comprises an enclosed area of a building.

13. The method of claim 1 wherein:
the contaminated location comprises a gas turbine engine in situ on an aircraft.

14. The method of claim 1 wherein:
the directing the discharge flow is a counterstream direction against a contaminant stream.

15. A decontamination method comprising:
directing at least a first flow of hydrogen peroxide to a catalytic reactor;
passing said first flow through a catalyst so as to decompose at least a portion of the first flow into water and oxygen; and
directing a discharge flow of said water and oxygen and additional hydrogen peroxide to a contaminated location so as to provide a decontamination,
wherein:
the directing the discharge flow is from an aircraft to the ground.

16. The method of claim 1 wherein the directing the discharge flow comprises:
decontamination of a first ship or land vehicle by a second ship or land vehicle.

17. The method of claim 1 wherein the contaminated location comprises one or more contaminants which comprise at least one of:
nerve agent;
blister agent;
live bacteria; and
bacterial spores.

18. The method of claim 1 wherein the contaminated location comprises one or more contaminants which comprise anthrax.

19. The method of claim 1 wherein:
the discharge flow has a mass flow rate of 2–9 kg/s for a duration of at least 10 s.

20. The method of claim 1 wherein:
the directing comprises aiming the discharge flow using an actuator.

21. The method of claim 3 wherein:
the bypass portion comprises 30–70% of the first flow.

22. A decontamination method comprising:
directing at least a first flow of hydrogen peroxide to a catalytic reactor;
passing said first flow through a catalyst so as to decompose at least a portion of the first flow into water and oxygen; and
directing a discharge flow of said water and oxygen and additional hydrogen peroxide to a contaminated location so as to provide a decontamination, the directing the discharge flow being a counterstream direction against a contaminant stream.

23. A decontamination method comprising:
directing at least a first flow of hydrogen peroxide to a catalytic reactor;
passing said first flow through a catalyst so as to decompose at least a portion of the first flow into water and oxygen; and
directing a discharge flow of said water and oxygen and additional hydrogen peroxide to a contaminated location so as to provide a decontamination, the discharge flow not recirculating back to the reactor.

24. The method of claim 23 wherein:
the contaminated location comprises an enclosed area of a building.

25. The method of claim 23 wherein:
the contaminated location comprises a gas turbine engine in situ on an aircraft.

26. The method of claim 23 wherein the directing the discharge flow is at least one of:
self-decontamination of a ship or land vehicle; and
decontamination of a first ship or land vehicle by a second ship or land vehicle.

27. A decontamination method comprising:
directing at least a first flow of hydrogen peroxide to a catalytic reactor;
passing said first flow through a catalyst so as to decompose at least a portion of the first flow into water and oxygen; and
directing a discharge flow of said water and oxygen and additional hydrogen peroxide to a contaminated location so as to provide a decontamination, wherein:
the first flow comprises at least 70% hydrogen peroxide by weight; and
the discharge flow comprises at least 30% hydrogen peroxide by weight, but less than the first flow.

28. The method of claim 27 wherein:
the first flow comprises at least 95% hydrogen peroxide by weight.

29. The method of claim 27 wherein the directing the discharge flow is at least one of:
self-decontamination of a ship or land vehicle; and
decontamination of a first ship or land vehicle by a second ship or land vehicle.

30. The method of claim 27 wherein:
the directing comprises aiming the discharge flow using an actuator.

\* \* \* \* \*